United States Patent [19]
Wallace

[11] Patent Number: 5,312,359
[45] Date of Patent: May 17, 1994

[54] INTRAVENOUS CANNULA INSERTION ASSEMBLY WITH PROTECTIVE SHIELD

[76] Inventor: Henry G. Wallace, c/o H. G. Wallace Ltd., Whitehall Road, Colchester, Essex C02 8JH, United Kingdom

[21] Appl. No.: 983,692

[22] Filed: Dec. 1, 1992

[30] Foreign Application Priority Data

Dec. 3, 1991 [GB] United Kingdom ............ 9125697
Feb. 28, 1992 [GB] United Kingdom ............ 9204357
Jul. 27, 1992 [GB] United Kingdom ............ 9215899

[51] Int. Cl.⁵ ............................................. A61M 5/00
[52] U.S. Cl. ........................................ 604/164; 604/198
[58] Field of Search ................... 604/110, 164–170, 604/198, 192, 263

[56] References Cited

U.S. PATENT DOCUMENTS

| | | | |
|---|---|---|---|
| 3,595,230 | 7/1971 | Suyeoka et al. | 604/164 |
| 4,832,696 | 5/1989 | Luther et al. | 604/164 |
| 4,850,961 | 7/1989 | Wanderer et al. | 604/53 |
| 4,909,793 | 3/1990 | Vining et al. | 604/164 |
| 4,917,669 | 4/1990 | Bonaldo | 604/164 |
| 4,944,728 | 7/1990 | Carrell et al. | 604/164 |
| 4,994,042 | 2/1991 | Vadher | 604/165 |
| 5,013,304 | 5/1991 | Russell et al. | 604/167 |
| 5,019,049 | 5/1991 | Haining | 604/165 |
| 5,102,394 | 4/1992 | Lasaitis et al. | 604/164 |
| 5,112,311 | 5/1992 | Utterberg et al. | 604/177 |
| 5,135,502 | 8/1992 | Koenig et al. | 604/164 |
| 5,171,231 | 12/1992 | Heiliger | 604/263 |
| 5,176,650 | 1/1993 | Haining | 604/164 |

FOREIGN PATENT DOCUMENTS 90102412.5 2/1990 European Pat. Off. .
US88/01146 3/1988 PCT Int'l Appl. .

*Primary Examiner*—John D. Yasko
*Attorney, Agent, or Firm*—Woodcock Washburn Kurtz Mackiewicz & Norris

[57] ABSTRACT

The present invention provides an assembly of an intravenous cannula insertion device and an elongate needle protector, said protector comprising a slotted tube, a needle and needle hub, said needle hub comprising a protrusion extending through said slot to allow the needle and needle hub assembly to be slidable within said protector, a cannula hub operatively inter-engagable with said needle hub within said protector, whereby said needle hub and said cannula hub are extensible together from the protector to allow i.v. insertion of the cannula, and wherein said assembly includes retraction prevention latches for preventing retraction of the cannula hub after it has been fully extended;

and wherein the cannula hub remains interlocked with the needle hub when fully extended until released from the assembly by a fin, so that needlestick is prevented.

7 Claims, 4 Drawing Sheets

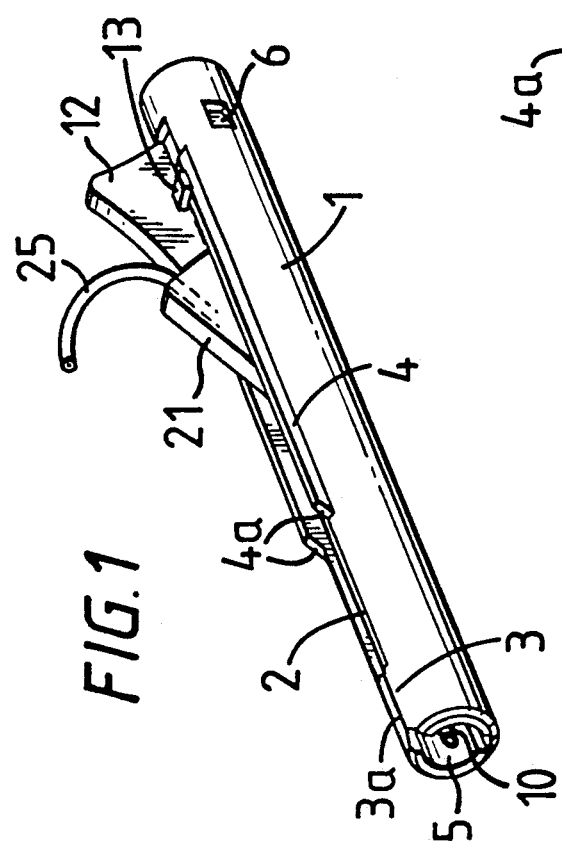
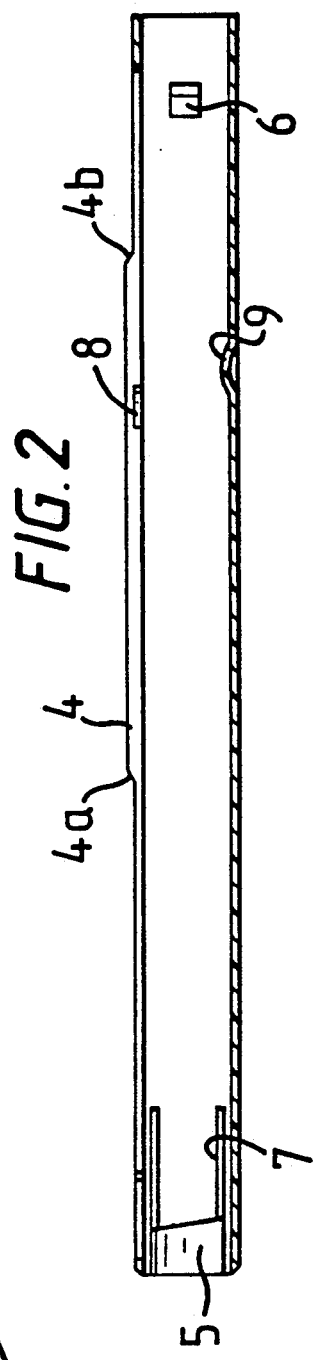
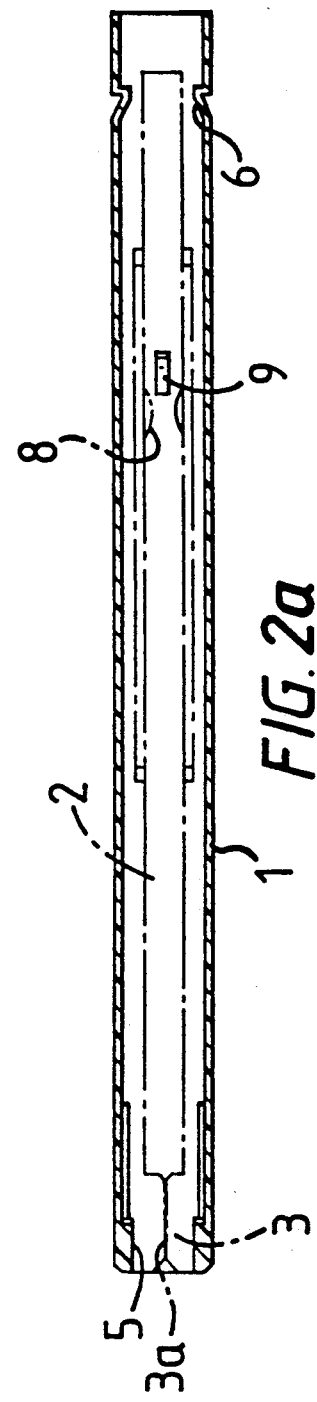

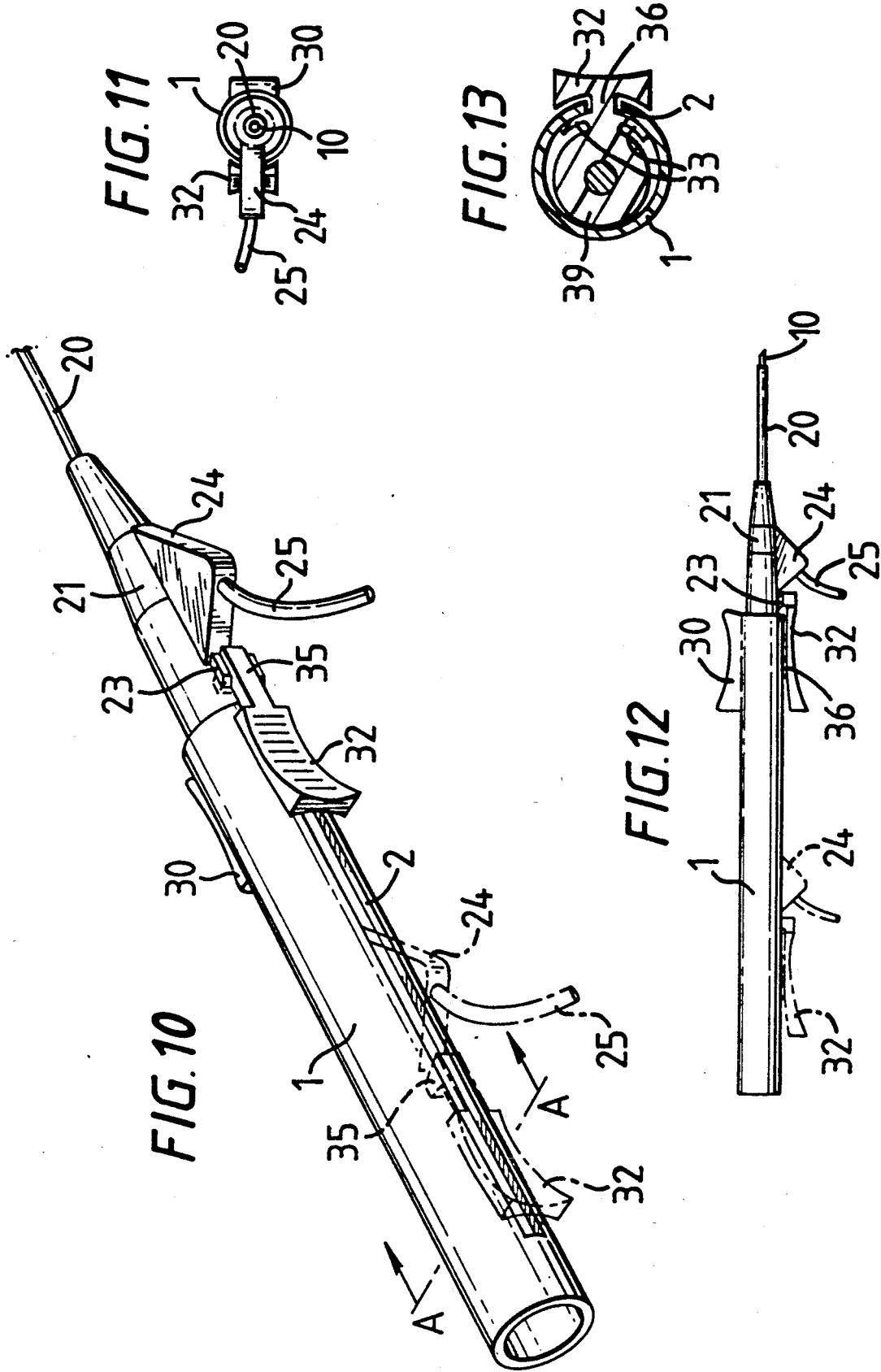

5,312,359

INTRAVENOUS CANNULA INSERTION ASSEMBLY WITH PROTECTIVE SHIELD

FIELD OF THE INVENTION

The present invention relates to a needle protector. Particularly this invention relates to i.v. catheter assemblies adapted to protect the sharp tip of a needle after use to prevent accidental injury from used needles.

BACKGROUND OF THE INVENTION

Typical over-the-needle i.v. catheter assemblies require the removal and disposal of a contaminated needle after the needle tip and catheter have been inserted into a blood vessel of a patient. Since at the time a needle is withdrawn, the user has other priorities, needles tend to be temporarily discarded for later disposal. This leads to the possibility of accidental scratching or pricking of health personnel which can lead to inadvertent infection with viruses such as HIV and hepatitis.

For this reason various attempts have been made to provide catheter assemblies incorporating various means for preventing a needle tip from coming into inadvertent contact with a user once the cannula hub of the catheter assembly has been left in situ in the patient.

One problem experienced with assemblies of this type is to provide a needle protector which protects the needle both before and after use by using the same elongate protector body. This body should allow a needle and needle hub to be assembled with a cannula and cannula hub within the protector body, said assembly being extended by sliding the same in the body to a position where the cannula hub is free of the protector as, for example, when inserted into a patient. The needle is then retracted within the body of the needle protector for safety.

Prior Art systems, however, allow the cannula hub and protector to be separated without initiating the withdrawal of the needle protector, thereby allowing the needle to become exposed if the device is not utilised properly.

In U.S. Pat. No. 5,019,049, there is described an assembly of an intravenous cannula insertion device and an elongate needle protector, said protector comprising;
 a slotted tube,
 a needle and needle hub, said hub comprising a fin protruding through said slot to allow the needle and needle hub assembly to be moved within said protector,
 a cannula hub operatively inter-engagable with said needle hub within said protector, whereby said needle hub and said cannula hub are slidable together in the protector to allow i.v. insertion of the cannula and wherein said assembly includes retraction prevention means for preventing the retraction of the cannula hub after it has been fully extended for use.

SUMMARY OF THE INVENTION

The invention provides in a first aspect an assembly of an intravenous cannula insertion device and an elongate needle protector, said protector comprising a slotted tube, a needle and needle hub, said needle hub comprising a protrusion extending through said slot to allow the needle and needle hub assembly to be slidable within said protector, a cannula hub operatively inter-engagable with said needle hub within said protector, whereby said needle hub and said cannula hub are extensible together from the protector to allow i.v. insertion of the cannula, and wherein said assembly includes retraction prevention means for preventing retraction of the cannula hub after it has been fully extended, and wherein the cannula hub remains interlocked with the needle hub when fully extended until released from the assembly by a primary release means.

The release means may be a primary release means associated with the needle hub fin which may be so adapted as to be utilisable by a single digit, of by means of squeezing pressure between the finger and thumb.

The release means may be provided with a first pressure face adapted to slide the assembly along the slot, and a second pressure face adapted to allow release of the interlock on single digit pressure. In a further embodiment the pressure faces may be combined as a single thumb profile. The assembly may further include a secondary release means operable subsequent to operation of the primary release means to allow the cannula hub to be freed from the assembly. The secondary release means may be actuated by a rotational movement of the assembly relative to the cannula hub.

The primary release means may be constituted by a needle hub fin which is integrally formed with the needle hub assembly, said fin being conjoined to the body of the needle hub by a generally centrally disposed hinge about which the fin may rock, said fin being spring-biased to an interlock position and provided with a detent for interengagement in the spring-bias position with a tab or pawl on the cannula hub. The fin may also be formed as a thumb profile which may rock about an eccentrically positioned hinge when the cannula hub is in its fully extended position.

The needle hub fin may also be provided with at least one lug adapted to ride upon a rail extending along a portion of the length of the slot whereby said fin is prevented from rotational movement about the hinge until it approaches the extended position. Alternatively the rails may optionally be dispensed with, in which case the lug or lugs are disposed to the interior of the needle protector thereby to retain the release means until the lugs clear the distal end of the protector and allow a rocking movement to release the cannula hub.

In a further form of the invention there is provided a needle protector tube comprising an elongate hollow body formed with a longitudinal slot to accommodate a cannula hub assembly and a needle hub assembly and having a length sufficient to accommodate an introducer needle.

The protective tube in accordance with the present invention is characterised in that the slot is open at its distal end and is provided with a nip portion to allow the passage of the cannula hub fin.

The distal end of the protector tube may be provided with a pair of opposed guide rails and a pair of inwardly directed lugs, said arrangement being adapted to require relative rotation of the cannula hub and the needle protector tube prior to their disengagement.

The slot may be provided over a portion of its proximal length with a pair of rails adjacent the edges of the slot, said rails acting to prevent release of the cannula hub from the needle hub fin in the proximal position. The proximal end of the tube may also be provided with at least one inwardly directed detent to retain the retracted needle hub. In a particular preferred form of the invention, the needle protector is provided with stop means for restraining the cannula hub against movement in the proximal direction.

DESCRIPTION OF THE DRAWINGS

The invention will now be described, by way of illustration only, with reference to the accompanying drawings wherein;

FIG. 1 shows a side elevation from above of an assembly of the invention;

FIGS. 2 and 2a show respectively vertical and horizontal cross sections thrugh a needle protector in accordance with the present invention, FIG. 10 shows a side elevation from above of a further embodiment of the invention, FIG. 11 shows a front view of the arrangement of FIG. 10, FIG. 12 shows a side view of the arrangement of FIG. 10, and FIG. 13 shows a section along a line "A—A" of FIG. 10.

DESCRIPTION OF PREFERRED EMBODIMENTS OF THE INVENTION

Figure 3:
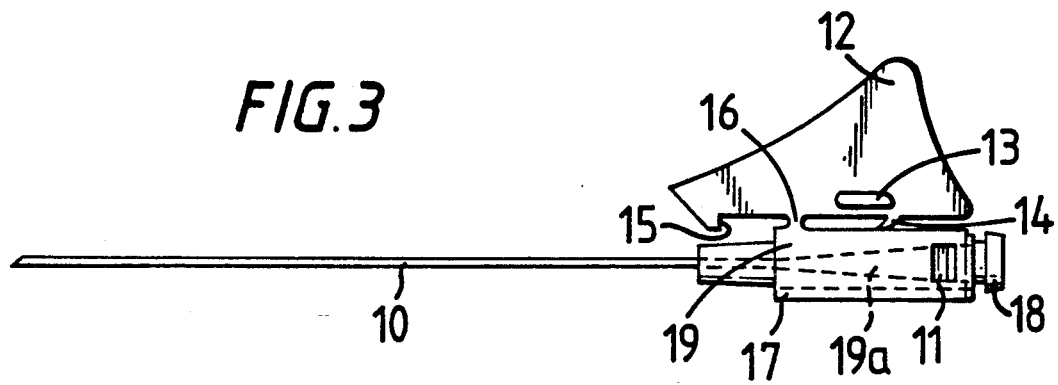
FIG. 3 shows a side elevation of the needle and hub for sliding co-operation in the assembly in the FIG. 1.

FIG. 1 of the accompanying drawings shows a needle protector having an elongate body (1) is formed of a plastics material with an elongate slot (2) along its intended upper edge. The needle protector (1) is adapted to accommodate within its hollow interior, a cannula and cannula hub (21) and a needle hub assembly (19) including a needle hub fin (12). The arrangement of FIG. 1 is shown in its at rest condition as may also be seen in FIG. 6.

The needle protector body (1) is moulded of a resilient plastics material and as best seen in FIGS. 2 and 2a provided with an elongate slot (2) extending from a closed proximal end to an open distal end. The distal end of the protector tube (1) is provided with a closed slit (3a) formed by a pair of inwardly directed cheeks (3). The needle protector is formed of a plastics material which is sufficiently resilient to allow the cheeks (3) to be pried apart to open the slit and allow the cannula hub fin to pass therethrough. The needle protector (1) terminates at its distal end with a pair of opposed luer lugs (5) which generally form the ovoid end surface of the needle protector (1), and a pair of opposed internal rails (7) extending generally parallel to the slot (2) and generally over the portion of the distal end of the needle protector body (1) adjacent the cheeks (3).

The protector body (1) is also provided with a pair of longitudinally extending rails (4) which extend over a major portion of the proximal end of the slot (2) for purposes which will be elucidated later. Disposed toward the proximal end of the needle protector body (1) are a pair of inwardly directed non-return latches (6). The sides of the needle protector slot (2) are also provided with inwardly directed locating lugs (8) for the purpose of retaining the assembly in its at rest condition prior to use. The internal floor of the hollow needle protector body is provided adjacent the locating lugs (8) with a needle protector stop (9). It will be appreciated that the needle protector body (1) is formed of a cheap plastics material since it exists essentially to protect the catheter needle prior to use and to be safely discarded subsequently.

Figure 4:
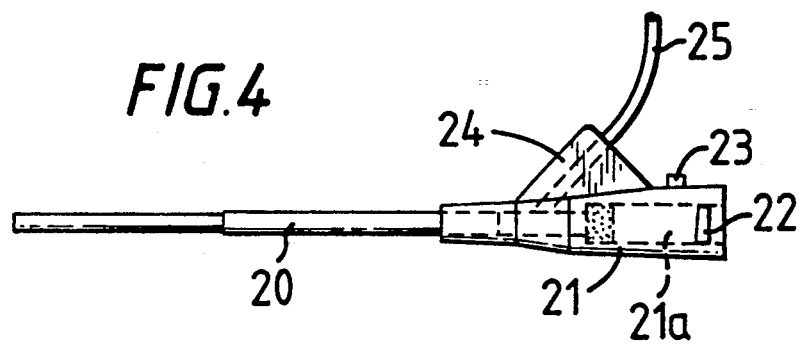
FIG. 4 shows a side elevation of a cannula and cannula hub for sliding co-operation in the assembly of FIG. 1.
Figure 5:
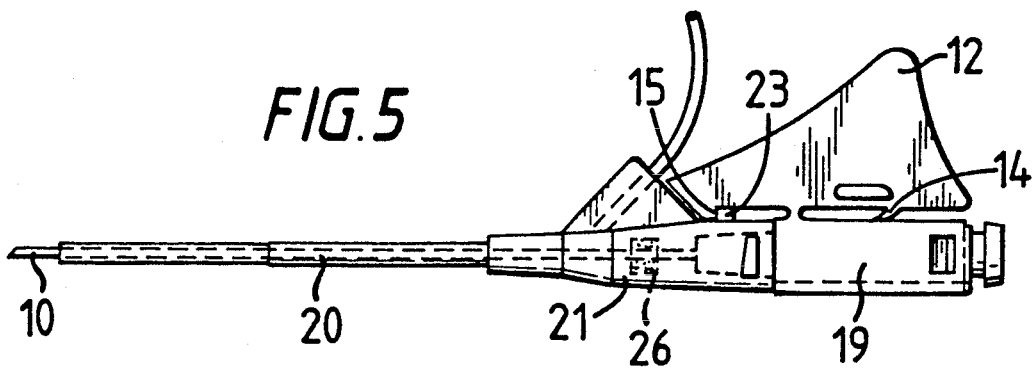
FIG. 5 shows a side elevation of an assembly of the elements of FIGS. 4 and 5 in operative interengagement.

With reference to FIGS. 3 to 5. FIG. 3 shows a needle and needle hub assembly for operative interconnection with a cannula and cannula hub assembly of FIG. 4; said assembly is shown in the inter-engaged condition in FIG. 5.

In FIG. 3, the needle (10) extends from a needle hub (19) in accordance with the usual practice in the Art. The needle hub (19) is provided with a flashback chamber (19a) shown in dotted lines in FIG. 3. The body of the needle hub (19) is also provided towards its proximal end with a pair of detents (11) adapted in use to co-operate with detents (6) in the needle protector (1).

The needle hub (19) is also provided on its uppermost surface with a needle hub fin (12) conjoined to the body of the needle hub (19) by means of a generally centrally located hinge (16). The needle hub fin (12) is also provided towards its forward end with a downwardly directed latch (15) and, remote from said latch and approximately equidistant from the hinge (16), with a moulded spring tab (14) adapted to forwardly bias the fin (12). The fin (12) is also provided on either side with perpendicularly directed ears (13) adapted in use to ride along the top edge of the rails (4) formed adjacent the slots (2) of the needle protector (1).

With reference to FIG. 4, the cannula (20) is provided with a cannula hub (21). The cannula hub (21) is provided on its upper surface with a cannula hub fin (24) provided, in this particular instance, with a side tube (25) for the cannula hub (21). The upper surface of the cannula hub (21) is provided to the rear of and adjacent, the fin (24) with a tab or pawl (23) for interengagement with the latch (15). The cannula hub (21) is provided with a cannula hub bore (21a) for accommodation of the needle (10) in accordance with the usual practice in this art. A sealing bung (26) is provided in the cannula bore (21a) for the usual purposes. The assembly is more generally shown in FIG. 5 wherein the fin (12) is biased by the spring bias (14) into interengagement with the detent (15).

Figure 6:
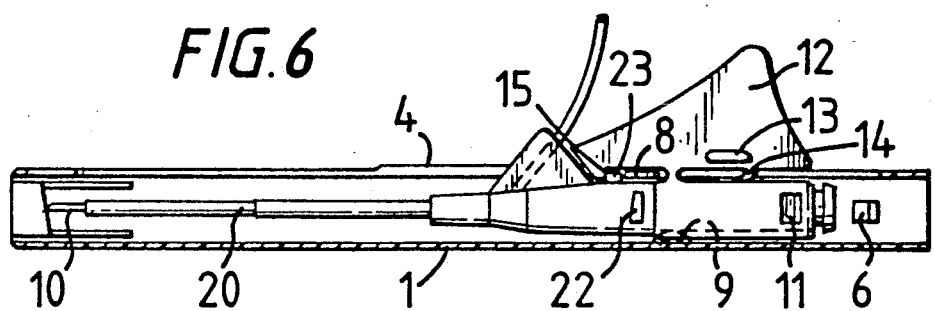
FIG. 6 shows a side elevation of the elements of FIGS. 3 to 5 in operative interengagement within the needle protector, in the at rest position.

With reference to FIGS. 6 to 9, it will be seen that the arrangement shown in FIG. 5 is disposed in its at rest condition in the protector body (1). The tip of the needle (10) is disposed within the needle protector body, while the rear of the cannula and needle hub assemblies is adjacent to, but forward of, of the non-return latches (6) disposed at proximal end of the needle protector body. It will also be noted, with reference to FIG. 6, that a needle protector stop (9) is upwardly disposed in the floor of the needle protector body (1) such that it contacts the rear end of the cannula hub (21). The needle hub (19) is provided, on its lowermost surface with a longitudinal channel (17) to accommodate the stop (9). Accordingly the assembly cannot slide backwardly while the needle hub assembly is inter-engaged with the cannula hub assembly. Further, locating hubs (8) locate the forward edge of the needle hub assembly thereby preventing the assembly from sliding forwardly until a significant pressure is exerted on the rearward face of the needle hub fin (12). The arrangement of FIG. 6 is provided in a sterile bag for protection before use.

Figure 7:
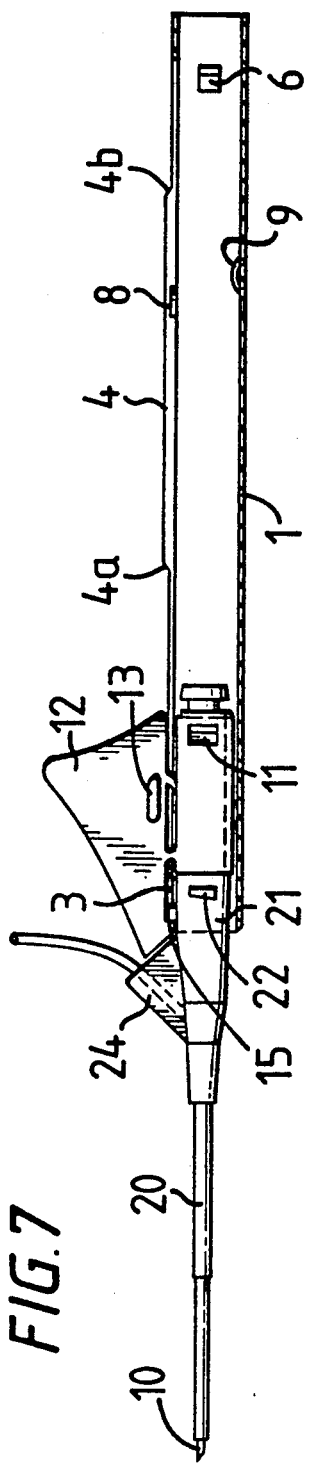
FIG. 7 shows side elevation of elements of FIGS. 3 and 4 in the extended position.
Figure 8:
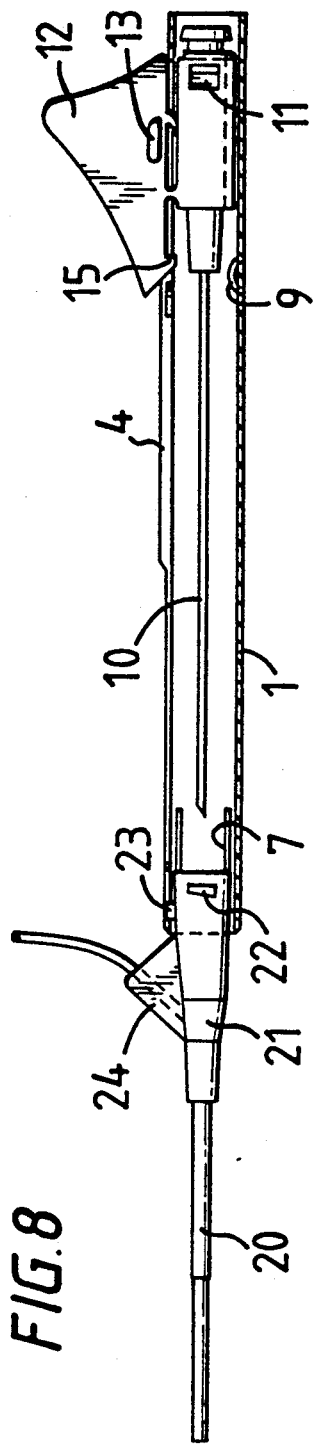
FIG. 8 shows a side elevation of elements of FIGS. 3 to 5 with the needle hub withdrawn.

In FIG. 7 it will be seen that the needle hub fin has been driven forwardly along the rail (4) to its extended position. In doing so, the ears (13) have cleared the forward sloping end faces (4a) of the needle protector body (1) such that now the fin (12) can rock anti-clockwise by means of digital pressure applied to the rear of the hinge (16).

The needle hub assembly can travel as far as the forward end of the slot (4) to the beginning of the closed slit (3a). In condition as shown in FIG. 7, the needle (10) extends from the cannula (20) so that the cannula can be inserted into the patient in the usual way. With the cannula successfully inserted and confirmed by means of the flash chamber (19a), it is then necessary to withdraw the introducer needle (10) as shown in FIG. (8). The withdrawal is effected by releasing the latch (15) against the spring bias of the spring (14) and withdrawing of the needle rearwardly until the detents (11) engage with the non-return latch (6) so that the needle is ready for disposal. In this condition the cannula hub (21) is still inter-engaged with the forward face of the needle protector (1) because luer lugs (22) cannot be withdrawn past the luer lugs (5) without relative rotation of the needle protector relative to the cannula hub (21). With this relative rotation completed, it is then possible to withdraw the needle protector from the cannula leaving the cannula in situ without the possibility of needle-stick.

Figure 9:
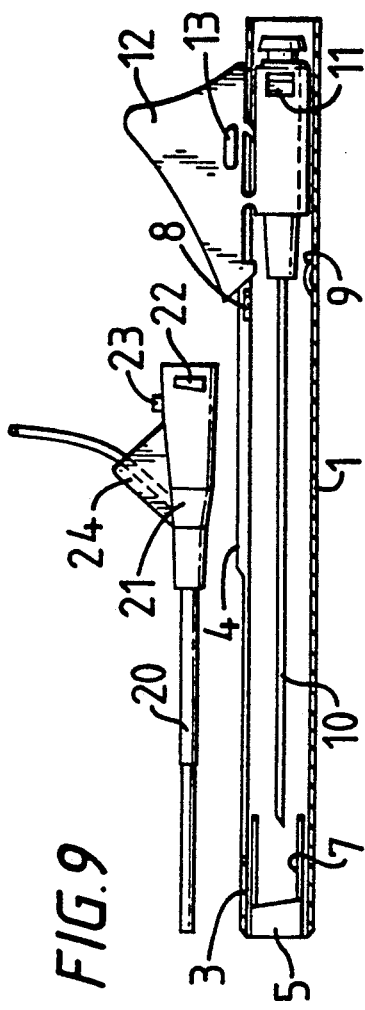
FIG. 9 shows a side elevation of the assembly in FIG. 1 with the cannula hub separated.

The final arrangement of parts is to be seen in FIG. 9.

The arrangement of the internal proximal latches prevents the needle from being extended as there are no means of releasing them once they are locked in place, and further the needle and cannula hubs are locked together as a unit and cannot be separated until they are extended from the sheath.

A further important feature of this device is that the sheath remains locked to the cannula until the needle is partially withdrawn (by releasing the tab on the cannula hub) thus providing a handle or gripping arrangement to facilitate insertion of the needle into the patient.

In a further form of the invention shown in FIGS. 10 to 13, an alternative form of locking the protrusion is shown.

It has been found that a number of surgeons like to bend the needle and the cannula assembly before insertion into the patient. This is to provide an angle for easier insertion of the device into a vein. As a result, when the needle is retracted into the needle protector, instead of being aligned straight in the needle protector sheath, its tip is likely to spring out from the slot because it is formed of a hardened metal and is inherently spring-like.

To overcome this problem, an alternative design is shown in FIGS. 10 to 13, which in effect requires relative rotation of the operational position of the needle protector through 90 degrees so that the slot is positioned in the horizontal rather than the vertical.

Accordingly, in FIGS. 10 to 13 like parts have been designated with like numbers and will not be described further except in so far as they impinge on the modus operandi of the device of FIG. 10.

With particular reference to FIG. 10, the needle protector body (1) is formed, as previously with a slot (2), although in the present instance the rails (4) have been removed.

A needle hub (39) is formed with a pair of internally extending lugs (33) (see FIG. 13), which are conjoined in turn to a profiled thumb grip (32) (which is substituted for the fin (12)). The profiled thumb grip (32) is provided with an eccentric hinge (36) and with a detent (35) to inter-engage with a corresponding pawl (23) on the cannula hub (21).

Additionally, the needle protector tube is provided diametrally from the profiled thumb grip (32) with a profiled finger grip (30).

In the at-rest position, as shown in FIG. 10 and 12 as ghost lines, the needle hub and cannula hub assembly are withdrawn to their protective positions prior to use. In use, the profiled thumb grip (32) is urged along slot (2), taking with it the cannula hub (21) in the fashion described with reference to FIGS. 1 to 9. At the point when the forward end of the needle hub extends beyond the end of the tube (1), the lugs (33) are cleared from retention within the slotted tube (1). In this last position the profiled thumb grip (32) may be rocked about the eccentric hinge (36) thereby disengaging detect (35) from pawl (23) on the cannula hub; allowing the cannula hub to be disengaged. This disengagement may either be direct, or may be via a secondary disengagement means which requires relative rotational movement if desired. It will be appreciated that the profiled thumb grip (32) cannot rotate about the hinge (36) until the lugs (33) have cleared the end of the protector tube.

By moulding a thumb grip or pad on the opposite side of the slot at the distal end of the sheath and said grips being an appropriate ergonomic shape for ease of grip and operation, it is more readily possible to utilise the device in the orientation shown in FIG. 10 so that when the cannula (20) and the introducer needle (10) are bent prior to insertion, and subsequently withdrawn, the needle will not tend to protrude from the slot (2).

Accordingly the invention provides an assembly of an intravenous cannula insertion device and an elongate needle protector, and separately, an elongate needle protector per se.

What I claim is:

1. An intravenous cannula insertion assembly comprising:

a cannula and cannula hub;

an elongate needle protector, said protector comprising a slotted tube;

a needle and needle hub, said needle hub and said cannula hub operatively inter-engageable within said protector, said needle hub and said cannula hub being extensible together from the protector to allow intravenous insertion of the cannula, said protector further having retraction prevention means for preventing retraction of the cannula hub after it has been fully extended; and interlocking means for interlocking the cannula hub with the needle hub both during extension and when fully extended until positively released from each other by a primary release means, said primary release means extending through said slot to allow the needle hub and cannula hub to be slidable within said protector, said primary release means being operable only when the cannula hub and the needle hub are in the extended position.

2. An assembly according to claim 1, further comprising a secondary release means to allow the cannula hub to be freed from the protector by rotational movement of the protector relative to the cannula hub.

3. An assembly according to claim 1, wherein the primary release means is a fin and said interlocking means comprises a detente on said fin and a tab or pawl on said cannula hub, said fin integrally formed with the needle hub by a hinge about which the fin may rock, said fin being spring biased to the interlock position with said detente engaged with said tab or pawl on the cannula hub.

4. An assembly according to claim 3, wherein said fin includes at least one lug adapted to ride upon a rail extending along a portion of the length of the slot of the needle protector, whereby said fin is prevented from rotational movement about the hinge until it approaches the extended position.

5. An assembly according to claim 1, wherein said fin includes at least one lug adapted to slide internally of the slotted tube, whereby said fin is prevented from rotational movement about the hinge until said internal lug or lugs clear the end of the tube when the cannula hub is in its extended position.

6. A needle protector tube for protecting a cannula and needle hub comprising, an elongated hollow body formed with a longitudinal slot to accommodate the cannula hub and needle hub and having a length sufficient to accommodate an introducer needle extending from said hub, said slot being open at a distal end and provided with a nip portion in said slot to allow for one way passage of a cannula hub fin to the extended position, the distal end of the protector tube further provided with retaining means for retaining the cannula hub in the extended position such that relative rotation of the cannula hub and needle protector tube is required to disengage the cannula hub and the needle protector tube.

7. A needle protector tube according to claim 6, wherein the slot is provided over a portion of its proximal length with a pair of rails adjacent the edges of the slot, said rails for preventing release of the cannula hub from the needle hub before the cannula hub and the needle hub are in the extended position.

* * * * *